US00PP12691P2

(12) United States Plant Patent
Scheffers

(10) Patent No.: US PP12,691 P2
(45) Date of Patent: Jun. 11, 2002

(54) DRACAENA PLANT NAMED 'KANZI'

(76) Inventor: Ruud A. M. Scheffers, De Plaats 9, 2675 CK Honselersdijk (NL)

( * ) Notice: Subject to any disclaimer, the term of this patent is extended or adjusted under 35 U.S.C. 154(b) by 0 days.

(21) Appl. No.: 09/327,606

(22) Filed: Jun. 8, 1999

(51) Int. Cl.[7] ..... A01H 5/00
(52) U.S. Cl. ..... Plt./383
(58) Field of Search ..... Plt./383

(56) References Cited

PUBLICATIONS

UPOV–ROM GTITM Computer Database, 2000/04, GTI Jouve Retrieval Software, citation for 'Kanzi'.*
UPOV–ROM GTITM Computer Database, 2000/04, GTI Jouve Retrieval Software, citation for cultivar name.*
Extract from the Register of Community Plant Variety Rights, 'KANZI', filed Jan. 16, 1998, File Number: 1997/0384, European Union (Grant No. E.U. 3756).

* cited by examiner

*Primary Examiner*—Bruce R. Campell
*Assistant Examiner*—Susan B. McCormick
(74) *Attorney, Agent, or Firm*—Foley & Lardner

(57) ABSTRACT

A distinct Dracaena plant named 'Kanzi' characterized by its longer leaves which are elliptic in shape with distinctive points; elongated plant growth; dark-green leaf margin (RHS 135A) which is approximately 0.5 cm wide at center of leaf; center leaf area which is dark-green (RHS 139A) to grey-green (RHS 191B and 1.5–2.5 cm wide in center of the leaf; and between the margin and center of the leaf is a white (RHS 155C) strip which is approximately 0.3 cm wide at center of leaf.

1 Drawing Sheet

BACKGROUND OF THE INVENTION

The present invention comprises a new and distinct cultivar of Dracaena plant botanically known as *Dracaena Vand. Ex. L fragrans* (group Compacta) and hereinafter referred to by the cultivar name 'Kanzi'.

The new cultivar was selected by the inventor, Ruud A. M. Scheffers, in Honselersdijk, The Netherlands, in September of 1994. The new cultivar was obtained as a mutation of *Dracaena Vand. Ex. L. fragrans* (group Compacta) 'Compacta Variegata' (unpatented). This new variety was a natural mutation, discovered as a sport in a cultivated area.

The new cultivar was first asexually propagated by the inventor in Honselersdijk, The Netherlands, in November of 1994. Subsequent asexual reproduction of the new cultivar by division has demonstrated that the combination of characteristics as herein disclosed for the new cultivar are firmly fixed and retained through successive generations of asexual reproduction.

BRIEF DESCRIPTION OF THE INVENTION

The following traits have been repeatedly observed and in combination distinguish 'Kanzi' as a new and distinct cultivar:

1. Longer leaves which are elliptic in shape with a distinctive point;

2. Elongated and less compact plant growth; and

3. Dark-green margin (RHS 135A) which is approximately 0.5 cm wide at center of leaf; center area which is dark-green (RHS 139A) to grey-green(RHS 191B) and 1.5–2.5 cm wide in center of leaf; between margin and center is a white (RHS 155C) strip which is approximately 0.3 cm wide at center of the leaf.

'Kanzi' is grown in a commercial greenhouse in temperatures of 20–21 degrees Celsius day and night. As with most Dracaena varieties, 'Kanzi' does not withstand direct sunlight so sun shields are used against bright sunlight. No artificial lighting or photoperiodic treatment is conducted. Highest temperature resistance is at least 40° Celsius and lowest is 5° Celsius. Compound fertilizer is added to the soil.

'Kanzi' has not been observed under all possible environmental conditions. The phenotype of the new cultivar may vary significantly with variations in environment such as temperature, light intensity, and daylength without any change in genotype. The following observations, measurements and values describe plants grown in The Netherlands under greenhouse conditions which closely approximate those generally used in horticultural practice.

In comparison with the well-known Dracaena cultivar 'Compacta Variegata', 'Kanzi' has 5–10% longer leaves which are darker green, grey/yellow-green in color. The center color of the leaves of 'Compacta Variegata' is grey, whereas the center color of the leaves of 'Kanzi' is grey-yellow. The leaves of 'Kanzi' grow more upright than those of 'Compacta Variegata'. 'Kanzi' grows more elongated than 'Compacta Variegata'.

BRIEF DESCRIPTION OF THE DRAWING

The accompanying photograph illustrates a plant of 'Kanzi' in its entirety following growth from cuttings under appropriate growing conditions, with colors being as true as possible with illustrations of this type.

DETAILED BOTANICAL DESCRIPTION

Color references are made to The Royal Horticultural Society Colour Chart (R.H.S.), except where general colors of ordinary significance are used. Colors are approximate as color depends on horticultural practices such as light level and fertilization rate, among others. Plants described are 16 weeks old.

Classification:

*Botanical.*—*Dracaena Vand. Ex. L. fragrans* (group Compacta).

*Commercial.*—Dracaena cv. Kanzi.

Parentage: Mutant from *Dracaena Vand. Ex. L. fragrans* (group Compacta) 'Compacta Variegata'.

Propagation: Primarily by vegetative division of the plant head or apical meristem.

Plant habit:

*Growth rate.*—Fast, approximately 1 cm per week.

*Form.*—Medium compact/slightly elongated.

*Plant height.*—Approximately 9–10 inches.

*Plant width.*—Approximately 12 inches.

Leaves:

*Form and size.*—Small elliptic to pointy, irregular curled; approximately 12 inches long and 2 inches wide.

*Texture.*—Strong and leather-like.

*Veins.*—One main vein, visible on the underside, RHS 136A to 191B.

*Color.*—Dark-green margin (RHS 135A) which is approximately 0.5 cm wide at center of leaf; center area which is dark-green (RHS 139A) to grey-green (RHS 191B) and 1.5–2.5 cm wide in center of leaf; between margin and center is a white (RHS 155C) strip which measures from approximately 0.3 cm to 0.5 cm in width at center of leaf, from the base to the tip.

*Margin.*—Slightly curled.

*Thickness.*—Medium.

*Number.*—Approximately 30 per plant when grown in a 4¾-inch pot for 150 days in The Netherlands.

Stem:

*Length.*—Short, approximately 0.5 inches.

*Thickness.*—Approximately 0.5 inches, formed by bases of leaves.

*Color.*—Dark-green (RHS 139A) in center to white to green/grey-green (RHS 189A) at edge.

Flowers: None observed.

Reproductive organs: None observed.

Roots: Orange-brown (RHS 175A to RHS 175B) in color; well branched; it takes approximately 3 weeks to initiate roots and approximately 7 weeks produce a rooted liner.

I claim:

1. A new and distinct cultivar of Dracaena plant named 'Kanzi', as described and illustrated herein.

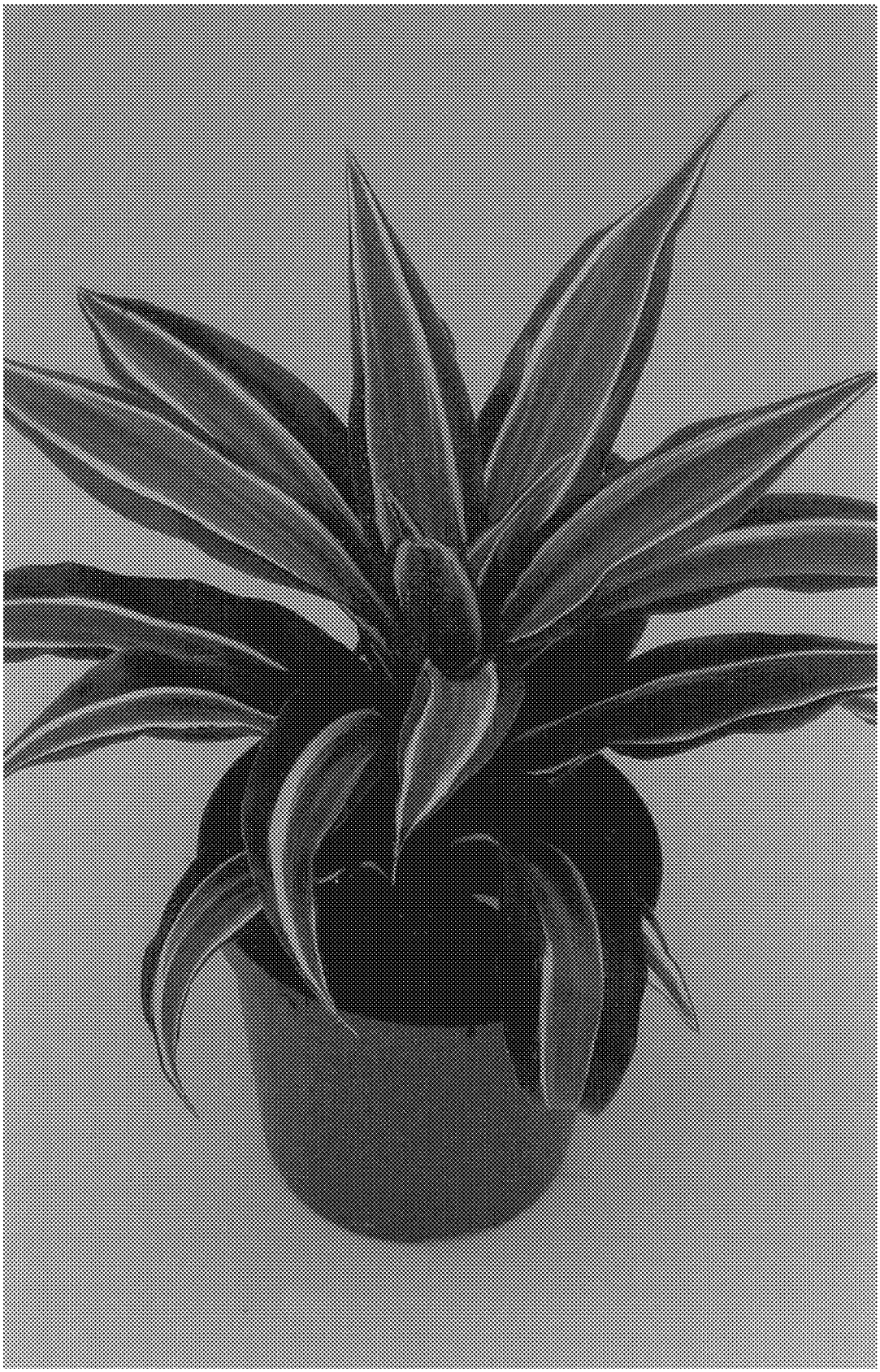

* * * * *